United States Patent [19]

Slimak

[11] Patent Number: 4,925,696

[45] Date of Patent: May 15, 1990

[54] PROCESSES FOR PRODUCTS FROM MALANGA

[76] Inventor: Karen M. Slimak, 9207 Shotgun Ct., Springfield, Va. 22153

[21] Appl. No.: 825,658

[22] Filed: Jan. 31, 1986

[51] Int. Cl.$^5$ .............................................. A23L 1/214
[52] U.S. Cl. ................................... 426/637; 426/518; 426/520; 426/523; 426/524; 426/552; 426/562; 426/601; 426/615; 426/640; 426/801; 426/804; 426/661
[58] Field of Search ................. 426/94, 518, 520, 637, 426/524, 640, 523, 552, 562, 601–602, 615, 640, 661, 801, 804

[56] References Cited

U.S. PATENT DOCUMENTS

| | | | |
|---|---|---|---|
| 91,554 | 6/1969 | Marshall | 426/637 |
| 310,927 | 1/1985 | Whitcomb | 426/637 |
| 1,194,455 | 8/1916 | Williams | 426/550 |
| 2,168,246 | 8/1939 | Shepherd | 99/81 |
| 2,469,995 | 8/1945 | Schaul | 99/207 |
| 3,615,658 | 10/1971 | Glabe | 99/17 |
| 3,767,424 | 10/1973 | Shimizu et al. | 426/372 |
| 3,881,028 | 4/1975 | Capossela et al. | 426/637 |
| 4,109,018 | 8/1978 | Thompson | 426/804 |
| 4,520,034 | 5/1985 | Ishii | 426/96 |

FOREIGN PATENT DOCUMENTS

| | | |
|---|---|---|
| A1517050 | 8/1974 | Fed. Rep. of Germany . |
| A2950315 | 6/1981 | Fed. Rep. of Germany . |
| A3141174 | 4/1983 | Fed. Rep. of Germany . |
| A1395654 | 2/1964 | France . |
| A2574633 | 6/1986 | France . |
| 104850 | 8/1980 | Japan .................. 426/639 |

OTHER PUBLICATIONS

Talburt et al., "Potato Processing", Avi Publishing Co., 1959, pp. 390–391.

Ware, Possibilities in New and Extended Uses of Sweet Potato, pp. 1–12 (1941).

The Oxford English Dictionary, 1933, Oxford, at the Clarendon Press, vol. VIII, pp. 1315, 1318.

Watt, B. K., Merrill, A. L., Composition of Foods, Agriculture Handbook No. 8, U.S. Department of Agriculture, 1963, pp. 51, 66–67.

Gove, P. B., ed., Webster's Third New International Dictionary of the English Language Unabridged, Merriam-Webster Inc., Springfield, Mass., USA, 1961, p. 1351.

Casier, J. P. J., et al., Bread Production from Pure Flours of Tropical Starchy Crops: III from pure and mixed flours of cassava, millet, sorghum, corn, rice, and the starches, in Inglett, G. E., and Charalambous, G., eds., Tropical Foods: Chemistry and Nutrition, vol. 1, Academic Press; NY, 1979, pp. 279–340.

Ciacco, C. F., Tubers: Composition and Use in Bread Making, Thesis, North Dakota State University School of Agriculture and Applied Science, 1977, 104 pp.

Rodriguez et al., Amylography of Plantain, Cassava, and Tanier Flours, Journal of Agriculture of the University of Puerto Rico, vol. LXVII, No. 3, pp. 303–310, 1983.

de Caloni and Cruz-Cay, Elaboration and Evaluation of Typical Puerto Rican Dishes Prepared with Mixtures of Plantain, Cassava and Tanier.

Flours, The Journal of Agriculture of the University of Puerto Rico, pp. 67–74, 1984.

*Primary Examiner*—R. B. Penland
*Attorney, Agent, or Firm*—Stevens, Davis, Miller & Mosher

[57] ABSTRACT

A variety of different food products, prepared from malanga, taro, amorphophallus and other plants of the family Araceae, are substitutes for wheat and other grains, milk, eggs, and a partial substitute for nuts.

14 Claims, No Drawings

PROCESSES FOR PRODUCTS FROM MALANGA

BACKGROUND OF THE PREFERRED EMBODIMENTS

1. Field of Invention

The present invention is concerned with the utilization of tubers of the malanga and all other plants producing tubers in the family Araceae, including taro and amorphophallus, with the purpose of producing various flours from the tubers, and other valuable edible products and industrial products.

2. Description of The Background

To increase the number of food products and forms of food products is of the greatest importance to persons with food allergies, and will become of even greater importance as food allergies are diagnosed in increasing numbers of people. As the potential problems of food allergies are more recognized, increasing numbers of people are looking for non-wheat items to include in their diets, to increase variety and aid in the prevention of food allergies.

Food allergies and intolerances have been known to exist for hundreds of years. The symptoms vary with each individual, and can include congestion, asthma, diarrhea, headaches, dizziness, joint pains, hives, eczema and in the most severe cases can cause anaphylaxis and even death. In recent decades, along with most other diseases related to the immune or auto-immune system, the incidence of food allergies has increased. In addition the number of foods to which a given individual reacts, and the severity of the reactions seems to be increasing. Indications are that food allergies/intolerances will continue to become increasingly more common and severe.

The need for new food sources and alternatives parallels the increase in food allergies. As the number of foods an individual can eat begins to dwindle, it becomes increasingly more difficult to maintain a nutritious, well-balanced diet from the foods remaining, and the search for new foods intensifies. For many food allergy patients, the allergy problem steadily becomes more severe as the patient is unable to avoid becoming malnurished.

There is, then, a real need for alternatives to the food products that are the common and accepted staples in the American diet. These food products need to be from hypoallergenic foods so they have the best chance of being well tolerated by the greatest numbers of people. The hypoallergenic food products need to provide acceptable substitutes for the most hyperallergenic food products—wheat, corn, and other members of the grass family, legumes, milk and milk products, eggs, nuts, and yeast.

The alternative food products should be from less common or less well known foods. Such foods will have been eaten less often, if at all, and there will be a lower chance for a person to have developed allergies to the new foods. Products from such uncommon foods could probably be tolerated by most persons, and the risk of developing allergies to the foods would be low.

The alternative food products need to be developed from foods in separate food families. This is important because food allergy patients can easily develop allergies to foods that are closely related to the foods they are already allergic to. New food products from as many new food families as possible (for example malanga products from the arum family), are much more needed than are food products from uncommon foods in a common food family (such as millet from the grass family). Alternative food products from food families not frequently included in peoples' diets will increase substantially the foods that people can eat in their rotation diets.

The alternative food products need to be highly concentrated foods. The above list of hyperallergenic foods includes most of the concentrated carbohydrates in the normal American diet. When people have to exclude these foods from their diets, the plant sources they have left to eat are primarily green leafy vegetables, tubers, and fruits. These food sources are high in fiber, but are relatively low in carbohydrates A person who must rely on potatoes or malanga as their main source of carbohydrates, must eat about 5 pounds each day. It is very hard for many adults to eat this much food, but it is even more difficult for allergic children who may have to eat almost as much.

The alternative food products need to be as close to the eliminated foods as possible, in form and texture For example, breads, pastas, cereal, cookies are needed from hypoallergenic sources, and these need to be as similar in taste and texture to their hyperallergenic counter parts as possible. This will make it possible for persons to enjoy foods they are used to, and will make them more likely to stay on their diets. Also people who are concerned that they may have food allergies are more likely to seek medical treatment if they know they will have pleasant alternatives in their diets.

Alternative food products are needed that consist of one primary ingredient, and this ingredient serves to replace wheat and other grains, milk, eggs, nuts, yeast, and sugar. The food allergies of individuals vary so greatly, that as the number of ingredients in a product increases, the number of individuals that can use the product decreases. Similarly, the products need to be free of additives, preservatives, and so forth, and should be completely free of pesticides and other chemicals.

Other characteristics that are important in new food products include convenience, portability, and variety. Many patients must change their diets at a time when they are very ill, and they simply do not have the strength to perform the food preparation needed when working with fresh fruits and vegetables.

A need, therefore, continues to exist for hypoallergenic food substances.

Until now there has been no alternative food product which could meet all of the above criteria. Many food products have been developed, but essentially all contain either wheat, or other grains, soy or legumes, milk, eggs, nuts, yeast, or sugar, or they don't have the characteristics of the common food products. Many specialty flours such as amaranth, have been combined with wheat flour to make new products, and these are not useful to the food allergic patient. Until now, there has been no attempt to completely replace wheat products with a non-grain flour source that also does not contain other main ingredients such as eggs, milk, sugar, and yeast.

There are few references to malanga, taro, amorphophallus and other tubers of the Arum family in the patent literature. U.S. Pat. No. 3,767,424 describes a method of separating starch from the tubers of Amorphophallus konjac, a tuber in the Arum family.

Taro is known for its use in production of poi, and frozen poi concentrates or rehydratable flakes are available in commerce. The starch of the malanga or taro is extracted, dried and pulverized to produce a starchy powder. Taro, starch powder malanga, starch powder and starchy powders of other tubers members of the Arum family, Araceae are used as one of several starches that comprise arrowroot starch.

Previous products of malanga flour were made by a high speed impact method which produced a flour of wide particle-size distribution, with the fibrous portions of the tuber remaining in the larger particle sizes, and rendering the flour unsuitably heavy and gritty. When screened, the larger particles were removed; this produced a lighter and less gritty flour, but one poorly suited for producing breads and other products where consistency and lightness are important. In addition it has been found that previous shreds had alhigh moisture content that made them susceptible to spoilage during dehydration and produced inferior products that spoiled easily.

It has now been found that a flour having reduced moisture content, improved fiber utilization, and more uniform particle size distribution can be prepared that will have improved storage capability and will provide products of palatabl consistency.

SUMMARY OF THE PREFERRED EMBODIMENTS

In the present imbodiment all references to "malanga" are intended to include malanga, taro, amorphophallus, and all other tubers in the Arum family.

It is one object of the present invention to provide flours and advantageous processes for producing flours from the malanga, taro, amorphophallus and all other tuberous varieties in the family Araceae.

Another object of the present invention to provide advantageous processes of producing valuable products from the flours of malagna and tuberous varieties of the family Araceae.

Another object of the present invention is to provide edible compositions of matter from the flour of malanga all tuberous varieties of family Araceae.

Another object of the present invention is to provide advantageous processes for producing substitutes for wheat products and other grain products.

Another object of the present invention is to provide advantageous processes for producing substitutes for milk, milk-products, and milk containing products.

Still another object of the present invention is to provide advantageous processes for producing substitutes for products containing eggs.

Still another object of the present invention is to provide advantageous processes for producing substitutes for legumes and legume-containing products.

Another object of the present invention is to provide advantageous processes for producing substitutes for nut butter products and products containing nut butters.

Another object of the present invention is to provide advantageous processes for producing substitutes for wheat, other grains, legumes, eggs, milk, and yeast-containing products using malanga flour as essentially the only ingredient.

Still another object of the present invention is to provide novel and advantageous processes for producing the following products with malanga flour as the only ingredient other than water, oil, salt, and leavening agent pastas, cereals, pancakes, bread, creamed cereals, cereal shreds, imitation nut butters, imitation mayonnaise, mashed potato substitutes, breads, bread crumbs, croutons, cookies, crackers, tortillas, chips, puffed chip-like products, corn bread, pie crust, pizza dough, dough-wrapped products, doughnuts, dumplings, hush puppies, pretzels, batter, milk, puddings, custards, light and heavy creams, condensed milk, muffins, waffles, french toast, crepes, and dry mixes for many products.

Another object of the present invention is to provide novel and advantageous processes for producing the following products with malanga flour as a primary ingredient: pastas, cereals, pancakes, bread, cakes, creamed cereals, cereal shreds, imitation nut butters, imitation mayonnaise, mashed potato substitutes, breads, bread crumbs, croutons, cookies, crackers, tortillas, chips, puffed chip-like products, corn bread, pie crust, pizza dough, dough-wrapped products, doughnuts, dumplings, hush puppies, pretzels, batter, milk, puddings, custards, light and heavy creams, condensed milk, muffins, waffles, french toast, protein coating batter, crepes, and dry mixes for many products.

Another object of the present invention is to provide advantageous processes for producing infant formulas Another object of the present invention is to provide advantageous processes for producing pharmaceutical products that are more effective for allergy patients by the use of hypoallergenic flours such as malanga flour as an inert ingredient.

Another object of the present invention is to provide advantageous processes for producing cosmetics containing cooked (preferable) or uncooked malanga powder as cosmetic base and facial powder, and other uses.

Briefly, these objects and other objects of the present invention as hereinafter will become more readily apparent can be attained by a plurality of method embodiments which employ a flour obtained from malanga tubers to prepare a variety of different foodstuffs.

Previous products of malanga flour and other tubers were made by a high speed impact method which produced a flour of wide particle-size distribution, with the fibrous portions of the tuber remaining in the larger particle sizes, and rendered the flour unsuitably heavy and gritty. When screened, the large particles were removed; this produced a lighter and less gritty flour, but one poorly suited for producing breads and other products where consistency and lightness are important. In addition it was been found that previous shreds had a high moisture content that made them susceptible to spoilage during dehydration and produced inferior products that spoiled easily It has now been found that a flour having reduced moisture content, improved fiber utilization, and more uniform particle size distribution can be prepared that will have improved storage capability and will provide products of palatable consistency.

DETAILED DESCRIPTION OF THE PREFERRED EMBODIMENT

The word malanga as used in this patent application is intended to include malanga, taro, amorphophallus and all other tubers of the family Araceae.

It has now been found that flour from malanga can be used in the production of many food products Moreover the flour can be used in every way wheat flour is used, although the processes are totally different.

Because malanga are frequently well-tolerated by people with multiple food allergies, and would be a highly nutritious, hypo-allergenic food stuff, we carefully investigated malanga and found that malanga, and all other tubers of the Arum family are well suited to multiple food products. The malanga is similar in size and shape to a white Russet potato, often being slightly smaller in girth The inside flesh is crisp but oozes a sticky latex like fluid, the flesh is generally white but may also be yellow, pink, or violet. The outer skin is hairy, and bulb-like in appearance The malanga in taste and texture after cooking is very similar to a white potato, but when cooling after heat treatment and gelatinization, the malanga becomes more firm. The malanga or taro is not well known in the U.S., except for its use in making poi, but it is appearing in produce departments of gourmet food stores where it is sold as a potato substitute. In tropical countries throughout the world, malanga, taro, etc are well known as yautia, cocoyam, eddo, coco, tannia, sato imo, amorphophallus. Common uses include: fu-fu, a very heavy paste eaten with soups and stews; poi; gravies and sauces from the starch; and heavy, taro rising breads where mashed vegetable paste is added to wheat and egg based dough mixtures.

While a previous product of malanga flour was made by soaking malanga tubers in water between the peeling and drying steps, it has now been found that the soaking step can be eliminated thus eliminating spoilage problems during drying steps and producing a flour of lower moisture content. Furthermore it was found that eliminating a high impact grinding method, produced a more uniformly fine flour which incorporates a greater proportion of the plant fiber into the flour, thus greatly improving the ability of the doughs to hold a rise and produce consistently uniform products.

In the preferred embodiment malanga and other tubers are subjected to any preprocessing steps of washing, scrubbing, cutting, rinsing and the like, peeled by any techniques of the art, peeling while clean (not recycled) water in passing over the tubers is preferred although malanga may also be processed unpeeled, rinsing (in distilled water is preferred although may be omitted), comminuting, slicing, chopping or any other technique desired (although not necessary) preferable shredding; dehydrating the material by air drying (at any appropriate temperature), freeze drying, vacuum drying or any other technique or combination of techniques of the art, preferably air drying, and pulverizing by such techniques as to produce a flour (with a moisture content of less than 15%, preferably 2-5%) that incorporates 20% or more of the plant fiber, preferably user 100% of the fibers, in other words, incorporates the entire tuber into the flour or other products produced.

In another embodiment, a partially or completely cooked flour may be produced in the method above with the added step of heating by any means available to the art in processes prior to, during, or after and in any combination with the processes listed above.

In the work with malanga, flour was made from the process described below. We began product development by following recipes for wheat flour, and making substitutions according to standard formulas given in allergy cookbooks for egg and milk replacers. The result was resound failures. Wheat-based processes could not be readily adapted for use with the new flour and were abandoned.

A cereal substance or constituent of cereal may be prepared from the dried shreds or particles of any shape of the malanga tuber, which are roasted, by any desired conventional technique (baked, toasted with or without oil).

Bread product and corn bread-like, muffin product can be prepared from malanga flour, water, and a small amount of salt (optional), oil (optional), and any conventional leavening agent in proportions ranging from 1:½ to 1:4, by weight, preferably 1:1.25 in processes of mixing at any desired speed, preferably a moderately high speed, shaping, and baking in any desired order or combinations of techniques common to the art. When a liquid sweetener such as a honey is used, the proportions range from 1:6:2: to 1:½:0 preferably 1:1.25:0.4: of malanga flour, water, and honey, and oil. The malanga bread is baked at temperatures ranging from 275°-550° F., preferably 425° F., for 15-90 minutes, preferably 40 minutes. The bread may also be prepared with any desired combinations of conventional ingredients including but not limited to other flours, extenders, binders, fillers, preserving agents, sweeteners, flavorings, seasonings, eggs, milk, nuts, and so forth.

In still another embodiment the bread product described above, and products such as corn bread, cookies, pancakes, muffins, and the like described in examples which follow may be used to prepare bread crumb and crouton-type and other similar products. Breads and the other products, in processes including but not limited to various orders and combinations of drying, toasting, coating, cutting, slicing, comminuting, and the like in steps conventional to the art may be used to produce bread crumb products with all possible uses of any other bread crumb products. These uses include but are not limited to: coating mixes for use alone or with batters, salad toppings, pie crusts, stuffings, and the like. They may also be prepared with any desired combinations of conventional ingredients including but not limited to other flours, extenders, binders, fillers, preserving agents, sweeteners, flavorings, seasonings, eggs, milk, nuts, and so forth.

By techniques in any desired order or combination of slicing, drying, roasting, toasting, baking, and the like, cubed products called croutons may be produced. These may be used on salads, soups, stews, stuffings, and any other ways croutons are used. The bread crumbs and croutons may also be prepared with any desired combinations of conventional ingredients including but not limited to other flours, extenders, binders, fillers, preserving agents, sweeteners, flavorings, seasonings, eggs, milk, nuts, and so forth.

In another embodiment, products the likes of pancakes, doughnuts, hush puppies, batter, waffles, and crepes can be prepared from combinations of malanga flour, water, oil, and small amounts of salt (optional), sweeteners (optional), and of any conventional leavening agents in proportions ranging from 1:6:⅓ to 1:½:0, by weight, the ranging from preferred proportions being 1:1½:1/7. These products are mixed, molded, shaped, fried, and so forth as appropriate for the product. The pancakes, doughnuts, hush puppies, batter, and crepes may also be prepared with any desired combinations of conventional ingredients including but not limited to other flours, extenders, binders, fillers, preserving agents, sweeteners, flavorings, seasonings, eggs, milk, nuts, and so forth.

In still another embodiment the above described pancake batter prepared as described earlier may be used as a pizza dough. In processes involving pouring the batter onto an appropriately shaped or sufficiently large surface, heating or baking in temperatures ranging from 375°-525° F., preferably 425° F., until dough is almost done but still tacky on the top, about 20 minutes. Add any desired ingredients including but not limited to various meats, cheeses, vegetables, spices, and other materials common to the art. Although any ingredients may be used, hypoallergenic ingredients might include ground precooked venison and nopales. Bake until dough is completely done and ingredients thoroughly cooked, about 10 minutes.

Alternatively, the toppings described above may be placed on the batter before cooking begins.

Alternatively, the above dough may be thoroughly baked, toppings added, and pizza reheated.

Alternatively the dough described for pie crust may be used as a pizza dough. The dough is prepared as described in the example, the dough is rolled out to the desired length, width, and thichness, toppings of any kind are added and the mixture is baked at 350° F. for 10-30 minutes.

In yet another embodiment, a product such as dumplings can be prepared from malanga flour, water, oil, and small amounts of salt (optional), sweeteners (optional), and any conventional leavening agent in proportions identical to those described previously for pancakes. Processes of combining ingredients and batter preparation are as described for pancakes. Teaspoon-sized portions of batter are dropped into rapidly boiling thickened water or broth for 2-6 minutes, preferably 5 minutes.

In yet another embodiment, a product such as waffles can be prepared from malanga flour, water, oil, and small amounts of salt (optional), sweeteners (optional), and any conventional leavening agent in proportions similar to those described previously for corn bread. The ranges of general proportions being $1:1\frac{3}{4}:1/12$. Processes of combining ingredients and batter preparation are as described for cornbread. Batter is then placed in waffle irons or other molds and heated by conventional means.

In another embodiment, a product such as french toast batter can be prepared from malanga flour, water, oil, uncooked, proteinaceous material, and a small amount of salt (optional) in proportions ranging from 5:14:8:8 to 1/10:12:0:0 by weight, preferably 1:14:2.4:2 in processes of gelatinizing the flour and water mixture, combining with remaining ingredients and blending with high speed blending equipment until smooth and homogenous. Material to be coated and prepared for french toast is preferably malanga bread, although any other bread or bread-like product may be used, and cooking is by any accepted technique. Alternatively batter may be prepared by the method above omitting the step of gelatinizing the flour-water mixture.

Alternatively, the proteinaceous material may be omitted, with the above proportions of flour and water remaining unchanged. The batter may be used alone, or in combinations with bread crumbs and other coating materials. The batter may also be prepared with any desired combinations of conventional ingredients including but not limited to other flours, extenders, binders, fillers, preserving agents, sweeteners, flavorings, seasonings, eggs, milk, nuts, and so forth.

In another embodiment, a product such as cookies can be prepared from malanga flour, water, oil, small amounts of salt (optional), sweeteners (optional), and small amounts of any conventional leavening agents in proportions ranging from 4:1:0 to 0.5:1:2, by weight, preferably 2.4:1:0.7 in processes of mixing, kneading, shaping, baking to produce cookies. Baking conditions range from 275°-500° F., preferably 350° F., and 2-40 minutes preferably 8-10 minutes.

Alternatively, when a liquid sweetener is used, the porportions are within the ranges described above, preferably 3:1:0.6 and 0.3 parts honey or other liquid sweetener per 1 part flour. Sweetener amounts may range from 0-1 part per 1 part flour.

Alternatively, add toppings as desired to the unbaked or baked dough. Any desired fruit, nuts, flavors, seasonings, sweeteners of the conventional art may be incorporated. The cookies may also be prepared with any desired combinations of conventional ingredients including but not limited to other flours, extenders, binders, fillers, preserving agents, sweeteners, flavorings, seasonings, eggs, milk, nuts, and so forth.

In yet another embodiment, crackers may be produced in any suitable machine for mixing heavy doughs through processes involving combining flour, water, and oil in proportions ranging from 3:1:4 to $\frac{1}{2}:1:0$, preferably $1\frac{1}{2}:1:1/5$ parts flour, water, and oil and small amounts of salt and leavening agents. In processes including but not limited to molding, rolling, cutting, and extruding, shape dough into desired cracker shapes. Dough may or may not be coated with a thin film of oil and salt. Any conventional heating method may be used, preferably 350° F. for 20 minutes. The crackers may also be prepared with any desired combinations of conventional ingredients including but not limited to other flours, extenders, binders, fillers, preserving agents, sweeteners, flavorings, seasonings, eggs, milk, nuts, and so forth.

In another embodiment of the invention a product such as tortillas or chips can be prepared by blending malanga flour with water, and then baking or frying the appropriately shaped dough. In preparing the mixture a range from $\frac{1}{2}:1$ to 2:1 amounts of flour and water are blended, preferably 1:1 flour and water. The dough may be cooked by any desired means including but not limited to frying with or without oil, and baking with or without a thin film of oil, following the conventions of the art.

In still another embodiment of the invention, a food product such as pie crust is prepared by blending malanga flour and oil in relative amounts of 0.4:1 to $1\frac{1}{2}:1$ parts water per unit part flour, preferably 0.9:1 parts water per one part flour, and 0.1:1 to 1:1 parts oil per unit part flour, preferably 0.3 parts oil per one part flour. Once the blend is prepared, it is kneaded, shaped or molded and baked if desired at temperatures ranging from 275° to 500° F., preferably 350° F. for from 2 to 45 minutes, preferably 10 minutes.

In yet another embodiment, doughs from processes described above for pie crust and pasta may be used to produce a puffed product by shaping the dough into flat, thin waters and frying the wafers in hot oil to produce a puffed or popped product. The dough may be shaped into a wafer or any other shape desired by combinations of extruding or other shaping means, rolling, cutting and other techniques in any order in any desired combination and fried. By this method shapes of a 'chip' or 'fry' may be obtained. Also long pieces may be shaped into a pretzel-like shapes and fried.

A puffed product may also be obtained when malanga flour is combined with pureed, cooked malanga. Although almost any desired combination may be used ranging from 5-100% flour, 0-95% cooked, and p, 0-50% water, the ratios for pie crust combined with an added 20% cooked pureed malanga is preferred. Either of the above processes may be used to produce very small-sized ⅛"-1" wafers, flakes and granules which can be used as a cereal product. Although for hypoallergenic purposes the above is preferred, any combination of flours, other tubers, other powdered vegetable material, extenders, binders, fillers, adhesives, antioxidants, preservatives, sweeteners, flavorants, spices and the like may be used with the above process.

In yet another embodiment of the invention, pretzels may be prepared from the doughs described for tortillas, chips, and pie crusts in processes of shaping, optional salting, and various combinations of baking with or without a thin coat of oil, frying, broiling, steaming, drying common in the food art to produce a pretzels of desired sizes and shapes. Additional embodiments include the pretzels above to which have been added to dough before baking or to the outside surface before or after baking, a variety of fillers, extenders, binders, flavorings, seasonings, preservatives and the like common to the art.

In yet another embodiment, the thick dough produced by the processes described in the preparation of pie crust may be used to produce dough encased or wrapped food products. The kneaded, thoroughly mixed dough may be shaped by extruding, rolling, cutting, and any other convenient technique to produce a variety of shapes onto which pureed fruit, cheese chopped meats, hot dogs, meat and vegetable combinations, cheese and the like may be placed. For example the thick dough may be shaped into 3×3×¼ inch squares onto which a pureed fruit such as sapote or carambola, and any other unusual or common fruit, are placed. These may be baked, broiled, or fried as is or 2 squares may be placed together such that the fruit forms a middle or inside layer in a sandwich-type effect. This may be baked, broiled, or fried to produce a product or may be frozen for sale to the consumer as a frozen product.

In another example, conventional art may be used to completely encase fruit or meat and vegetable mixtures. The dough covered product which may have any shape, commonly an ovoid shape ranging from 1 inch to 6 inches in length may be baked, boiled, broiled, fried and so forth in any conventional means to produce good tasting, convenient foods.

The dough may also be used in pot pie-type products.

In another example, pureed or flaked meat may be combined with a small amount of imitation mayonnaise in approximate proportions of 2:1 and placed on a 6×6×¼ inch dough square. The dough is rolled around the meat mixture to form a tamale-like shape. This product may be baked, broiled, fried, or frozen. If uncooked meats are used, the product should be cooked by means other than frying. The dough-wrapped products may also be prepared with any desired combinations of conventional ingredients including but not limited to other flours, extenders, binders, fillers, preserving agents, sweeteners, flavorings, seasonings, eggs, milk, nuts, and so forth.

In another embodiment, malanga flour may be combined with a vegetable oil such as sunflower oil, olive oil, or the like in an amount ranging from ½:1 to 4:1 parts by weight flour per part by weight oil, preferably 1.8:1, to which is added a gelatinized water-flour mixture which contains flour and water in proportions ranging from 1:1 to 1:30, preferably 1:5.4.

The flour/oil mixture and flour/water mixture are combined in amounts by volume ranging from 20:4 to 20:0, preferably 20:1.

The flour may be combined with various ingredients to prepare a colloidal product having the consistency of mayonnaise. The mayonnaise-like product itself is rather bland in taste, and it takes on the flavoring characteristics of the material(s) blended with it in its end use—e.g. tuna fish, potato salads, sandwich meats. Flour, water, and oil are combined in ratios of 0.5–3:1–15:0–15, preferably in ratios of 1:8.6:3.8. The flour and ¼ to all of the water, preferably all of the water are combined and heated by any convention of the art to such temperature and for sufficient time to completely gelatinize the starch granules. This mixture in steps of cooling (optional) and high speed blending with any remaining water, and oil to produce a colloidal product to which may be added any acid, such as lemon juice, citric acid, ascorbic acid, acetic acid and the like in amounts ranging from 0–2 parts acid to 1 part original flour used, about 0.6:1 is preferred.

The mayonnaise has the colloidal properties of mayonnaise, with no other added ingredients. This is not to preclude the use of other ingredients commonly used in the food art, including but not limited to eggs, milk, other flours and starches, sweeteners, flavors, seasonings, and spices of any kind.

The mayonnaise produced by the above process has the advantages of being able to be frozen and thawed without destroying or significantly altering the colloidal properties of the product.

In another embodiment of the invention custards-type products may be produced. When flour and water are combined in proportions ranging from 1:1 to 1:30, preferably 1:6, and heated with stirring until gelatinized to a thick paste-like glue and subjected to blending in high speed blending device with the addition of oils in proportions ranging from 0:1 to 3:1, preferably ⅓ part oil per 1 part original flour by weight, this process produces white, creamy fluids of various thicknesses with properties similar to evaporated milk, which when allowed to stand with or without cooling, will solidify to produce products with properties very similar to custards. These custard-type products may be used without modifications as custards. In another embodiment the fluids may be combined with vegetables such as peas, corn, and squash to form custards commonly called corn puddings and the like. The fluid may be combined with pureed vegetables such as corn, pumpkin, and squash to produce custard-like pies, and with fruits such as peaches, apricots, coconut, and bananas to form creamed pies and the like.

One of the advantages of these products is that they do not require further cooking to produce the "setting up" and when combined with precooked vegetables, etc. do not need additional baking or other heat treatments. The custards may also be prepared with any desired combinations of conventional ingredients including but not limited to other flours, extenders, binders, fillers, preserving agents, sweeteners, flavorings, seasonings, eggs, milk, nuts, and so forth, but they are not necessary to achieve the desired product.

In another embodiment of the invention, a product such as a pudding can be prepared by blending flour, water, oil, and pureed fresh malanga paste in proportions ranging from 1/7:10:6 to 1/7:½:1/10, preferably about 1/7:2:1. The product is produced in processes where as a first process step the flour and from 10 to 100%, preferably 50% of the water are combined and heated by any convention of the art to produce a thick gelatinized paste. This paste is then combined with the remaining raw materials and blended to a smooth, homogenous, mixture by conventional mixing techniques. With the addition of no additional ingredients the product has a sweet, pleasant taste. However, this is in no way intended to preclude the use of other constituents commonly used in puddings including but not limited to any desired combinations of conventional ingredients including but not limited to other flours, extenders, binders, fillers, preserving agents, sweeteners, flavorings, seasonings, eggs, milk, nuts, and so forth.

Alternatively, a pudding-type product may be prepared using flour and water only, in proportions ranging from 1:1 to 1:30, preferably 1:5.4. The ingredients are combined, heated by any conventional techniques until the mixture is completely gelatinized. Cool to between 35°-0° C., preferably 10°-20° C. until the consistency of pudding.

In still another embodiment, in processes as are described for pancakes; flour, water, oil, and small amount of leavening agent, and salt are combined in proportions preferably of 1:2:1/7, but ranging from 1:4:0 to 1:1:½ to produce a crepe-type product. The batter may be used by techniques known to the art in cooking and using the malanga crepes. The may also be prepared with any desired combinations of conventional ingredients including but not limited to other flours, extenders, binders, fillers, preserving agents, sweeteners, flavorings, seasonings, eggs, milk, nuts, and so forth.

In still another embodiment of the invention, when a given amount of malanga flour is mixed with water of a temperature range from 0 to 150 degrees C., boiling water is preferred in proportions ranging from ½ to 4 parts of flour per part water, preferably 1½ parts flour to one part water, a dough can be prepared, which, after maintaining a heating and kneading period of from 0 to 10 minutes, preferably 2 minutes, followed by extruding, cutting and drying, prepares such products as noodles, pastas and the like. It is also possible to mix the batter prepared with baked malanga or other farinaceous and mealy textured tubers and possibly other vegetable matter in the amounts to produce stiff doughs for gnocci, hard dumplings, and other pasta products. In another embodiment of the invention, a thick gelatinized paste of cooked malanga flour and water comprised of preferably 1:6 parts flour and water, with acceptable ranges of 1:2-30, may be added to the above described dough mixture before extrusion to any desired pasta shapes, to produce substitutes for egg based pasta.

In a further embodiment of the invention, the pasta doughs described above, with or without the egg-substitute may be heated at temperatures above 50° C. for 2-30 minutes, preferably 2-5 minutes at 95° C. to gelatinize a part of all of the dough prior to extrusion.

The pastas thus described are dried by any conventional means, preferably air dried on trays to produce a final product.

In its final uses, this pasta does not swell significantly beyond its dried size, when cooked in boiling water and the like. This is due to the fiber content which has been retained in the flour. These fibers prevent the typical swelling and conversion to a jelly-like mass common to noodles from most pure starches. Thus these pasta products retain a form and consistency similar to wheat based noodle products. They may be used in all ways any other noodles are used.

In another food embodiment, the malanga flour can be combined with water in a ratio of 12:1 to 3:1 parts by volume water per unit volume of flour, preferably 5:1 water to flour, and a small amount of a vegetable oil to produce a malanga milk. Preferably ¼ of the flour and water are combined (actual amounts may range from 10-80% flour and 25-100% water), heated by conventional methods until the mixture is completely gelatinized. The gelatinized mixture and remaining ingredients are combined, thoroughly mixed in a high speed blending device to produce a malanga milk or other similar fluid mixtures.

In the above embodiment, flour of almost any particle size may be used ranging from very coarse to very fine. The particle size is not important for that portion of the flour used for gelatinization, although fine flours are preferrable. A more finely divided flour product is desired for the flour that remains uncooked in the milk. The smaller the particle sizes, the better, preferably at least less than 0.001 inch. The milk produced from very fine flours does not require straining to yield a smooth homogenous product. Larger particle sizes produce a gritty product that must be strained before use. The larger the particle sizes, the greater proportion of malanga flour that is removed by straining, and the more separation into layers that occurs on setting.

In a preferred embodiment cooked malanga flour, water in proportions of 1:2 to 1:8, with preferred proportions being 1:4 may be combined together with small amounts of salt to product a milk-like product. In another food embodiment, malanga flour can be combined with water in a ration of 1:1 to 30:1 parts by volume of water per unit of flour, preferably 3-6:1 water to flour, and a small amount of a vegetable oil. 50 to 100 percent of the flour is combined, and heated until the mixture is completely gelatinized. The gelatinized mixture and remaining ingredients are combined, thoroughly mixed in a high speed blending device to produce substitutes for light to heavy creams and condensed milk.

In other embodiments of the invention, the finely divided flour may be employed as a thickener, filler, or extender in the preparation of hypoallergenic cosmetics, and industrial products. For example, malanga flour preferably a precooked product of fine particle sizes may be used in dusting powders and face powders. Various shades may be obtained by heating and toasting methods. This produces a face powder product which could be well tolerated because people would be only placing nonallergic items on their faces. Similar powders may also be used as bases for liquid and paste make-ups to produce hypoallergenic products. The cosmetic preparations may also be prepared with any desired combinations of malanga flour with conventional ingredients including but not limited to other flours, extenders, binders, fillers, preserving agents, and so forth.

In another embodiment, the dried shreds from peeled or unpeeled, preferably peeled, cooked malanga may be used to produce a shredded cereal product.

The flour from dried, cooked malanga of various particle sizes may be coarsley ground to produce a creamed cereal product and finely ground to produce instant mashed malanga products. In final use, each product is combined with water in ratios of 1:2-10, preferably 1:5, heated for 2 to 10 minutes at temperatures from 75° to 100° C., preferably 100° C. in processes of rehydration and heating.

The cooked malanga flour ma also be used in combination with the raw malanga flour in many of the products and processes described previously, and may also be used with many other types of flours.

Yet another embodiment involves processes to produce a hypoallergenic infant formula. Many infants are unable to tolerate the currently available infant formulas. Infants unable to tolerate the grains, legumes, milk products eggs, and grain-derived sugars listed earlier along with coconut oil are almost certainly going to be intolerant of all commercially available infant formulas. These infants are usually unable to tolerate breast milk because of allergies to digested food residues in the milk. The parents of these infants desperately seek alternatives and usually end up using cooked purees of tubers and other foods. There is a real need for infant formulas without grains, grain-based sugars, legumes, milk and milk products, and coconut or corn oil. No truly hypoallergenic formula exists at present.

The earlier described process for producting malanga milk, in which finely powdered, precooked, dried malanga flour is substituted for the raw flour in the second step of the process may be used to produce infant formulas. In one infant formula embodiment the just described formula is used without further modification in either full fluid form, condensed form, or dry powdered form as a hyperallergenic formula to which the user would add appropriate amounts of protein and fat per quart of fluid fully reconstituted. This would be ideal for many infants since the protein and fat sources could be varied by the parents according to the physician's instructions and specific allergies of the infant. This would assure the broadest tolerance of the formula.

The tubers such as malanga are highly nutritious in vitamins and minerals, and because they are almost universally well tolerated, malanga is an excellent choice as a base for hypoallergenic formulas.

In another embodiment of the invention, a more complete infant may be obtained by adding appropriate amounts of protein and carbohydrates to the above described formulas. Any protein and fat source is included in the embodiment as part of the product and process, preferably for hypoallergenic purposes beef, milk, pork, eggs, lamb, goat, and legume sources would not be used, obscure protein sources such as venison, rabbit, even fish are much more suitable, as fat source sunflower oil is preferred although any oil or other desired fat source can be used. By conventions of the art formula available as ready-to-feed, liquid concentrate, and dry powder, and any other form are included in the embodiment.

Many variations in the above formula by varying amounts of oil, water, malanga, added ingredients and so forth, all are hereby included in the embodiment. The infant formula may also be prepared with malanga flour and combinations of conventional ingredients including but not limited to other flours, extenders, binders, fillers, preserving agents, sweeteners, flavorings, seasonings, eggs, milk, nuts, and so forth. These are hereby included in the embodiments.

In another embodiment, malanga flour may be used in a wide variety of pharmaceutical products as a hypoallergenic filler, extender, and inert ingredient. The use of a hypoallergenic material for these purposes would eliminate allergic reactions that food allergic patients may have to the nonactive ingredients, would thereby enhance the number of persons who tolerate the drugs and could help the medications to be more effective for the allergic patient.

Many of the products described above are well suited for the preparation of packaged dry mixes, frozen products and the like, all such products and processes are incorporated with this embodiment.

As is evident from the above discussion, the central objective of the present invention is to provide a variety of different foodstuffs, the basis for all of which is a tuberous plant, which is well tolerated by many persons with multiple allergies, hence the term hypoallergenic. Thus, insofar as the flour obtained from the tuber is mixed with other ingredients which do not detrimentally affect the hypoallergenic properties of the food product obtained, hypoallergenic foodstuffs of different sorts can be obtained by the techniques described above. On the other hand, it is recognized that other ingredients can be added to the flour used in the present invention which may destroy the hypoallergenic nature of the food-stuff being produced, but yet which produce useful foodstuffs of still different qualities. The present invention also embraces these hyperallergenic foodstuffs, and therefore the present invention is not limited to just hypoallergenic foodstuffs.

Having generally described this invention, a further understanding can be obtained by reference to certain specific examples which are provided herein for purposes of illustration only and are not intended to be limiting unless otherwise specified.

EXAMPLE NUMBER 1

Malanga Bread

Place 453 g malanga flour in a suitable conventional mixing device. Slowly add 566 g water while mixing at lowest speed. When well blended, mix at highest speed for about 1 minute. Stir in 35.4 g baking powder; then mix at high speed for 15 seconds. As fast as possible pour into baking pan. Carefully place in oven heated to 425° F. and bake for 40 minutes. The amount of water needed varies with the moisture content and particle size of the flour. More coarse flour and/or flour with a lower moisture content will require more water. The resultant malanga bread product may be used in any way wheat bread is used.

EXAMPLE NUMBER 2

Malanga Imitation Corn Bread

Ingredients: 453 g malanga flour, 566.25 g water, 35.4 g malanga baking powder. Combine above ingredients with baking powder added last; mix well, at highest speed with conventional mixing equipment until well blended and uniform consistency, about 1 minute. Transfer quickly into suitable baking container and bake 30–40 minutes at 425° F.

Alternatively, the following proportions may be used in an imitation corn bread with honey or other liquid sweetener: 453 g malanga flour, 566 g water, 150 g honey, 35.4 g malanga baking powder. This product is used in the production of cake doughs.

EXAMPLE NUMBER 3

Malanga Muffins

Combine 453 g malanga flour, 566 g water, 12:5 g oil, 35.4 g malanga baking powder and mix well, at high speed with conventional techniques of the art until smooth and well blended. Add 23.6 g baking powder and mix well. Pour quickly or transfer by other means into suitable baking equipment. Bake for 20–25 minutes at 425° F.

EXAMPLE NUMBER 4

Malanga Pancakes

The following ingredients: 336.9 g malanga flour, 453 g water, 6.5 g salt, 50 g oil, 8 g malanga baking powder, are combined and mixed well on highest speed, preferably 1–2 minutes in high speed blending device. Batter may be transferred to suitable baking or frying device, device to be prepared as required by the art, preheated on medium-high heat. Dough may be cooked in sizes ranging from dot sizes to several feet across. Turn when top surface has turned dull and the bottom surface is golden brown in color.

EXAMPLE NUMBER 5

Malanga Pancake Mix

To provide an example of a dry mix-type product, malanga pancake mix is used. A malanga pancake mix product can be made by combining ingredients: 453 g flour, 87 g salt, and 10.7 g malanga baking powder. Mix ingredients well in a rolling ball mill or other conventional means to form a dry mix. Pancakes can be made from this dry mix by the addition of water and water/oil mixtures.

Alternatively, by conventions of the art, the pancake mix oils may also be added to the above ingredient mix to produce a dry mix that contains oils. Also, sweeteners, flavors, seasonings, binders, fillers, and so forth may be utilized in the production of malanga pancake mixes.

EXAMPLE NUMBER 6

Pizza Dough

The batters described in Example 4 may also be used as a pizza dough. Prepare batter as described above, pour dough onto pizza pan. Place in oven and bake at 425 degrees until dough is almost done but still tacky on the top, about 20 minutes. Add any desired ingredients various meats, vegetables, spices, and other materials common to the art. Bake until dough is completely done and ingredients thoroughly cooked, about 10 minutes.

Alternatively, the topping can be placed on the batter before cooking begins, or after cooking ends. Alternatively, the dough described for pie crust, Example 14, may be used as a pizza dough. The dough is prepared as described in the example, the dough is rolled out to the desired length, width, and thickness, toppings of any kind are added and the mixture is baked at 350° F. for 10–30 minutes.

EXAMPLE NUMBER 7

Malanga Waffles

The following ingredients are combined by the method described above in Example 5:336.9 g malanga flour, 453 g water, 6.5 g salt, 50 g oil, 8 g malanga baking powder. Pour batter into waffle iron or other suitable molding or shaping device preheated to 300°–500° F. Watch for steam coming from the waffle iron as the waffles cook. Leave waffle iron closed as long as steam can be seen rising from the waffle iron. When steam stops, all water has been baked out of the batter and waffles are done, 5–10 minutes or more. When done the waffles should be golden brown in color.

EXAMPLE NUMBER 8

Malanga French Toast

Combine 21 g malanga flour, 3.25 g salt, and 297.5 g water and mix until smooth and homogenous. Heat by any desired convention until mixture is well gelatinized and thickened. Stir in 50 g oil. Pour mixture into high speed blending device; while blending at high speed, slowly drop in ground meat or other protein source and blend until meat is completely pulverized and liquefied. Alternatively, cook 226.5 g water and 21 g malanga flour until well gelatinized and thickened.

Coat pieces of malanga bread. Fry to slightly browned and crusty in lightly greased griddle or skillet preheated to medium high. Alternatively french toast batter may be prepared by the method as described above without cooking the flour/water mixture.

French toast batter may be used for many combinations with malanga bread crumbs and many other coating materials or alone.

EXAMPLE NUMBER 9

Malanga Cookies

Combine and mix well by the conventional art: 505.4 g malanga flour, 210.6 g water, 6.5 g salt, 150 g oil, 18 g malanga baking powder. Form into cookie shapes by the conventional art, preferably very thin. Bake at 350° F. on ungreased surface for 8–10 minutes, or until a light golden brown on the underside. Alternatively, add toppings as desired to the unbaked or baked dough. Any desired fruit, nut, flavors, seasonings of the conventional art may also be used.

When a liquid sweetener or honey is used, the following ingredients are combined as described above: 505.4 g malanga flour, 170 g water, 1.6 g salt, 150 g honey, 150 g oil, 18 g malanga baking powder.

EXAMPLE NUMBER 10

Malanga Doughnuts, Pretzels, Hush Puppies, Doughnut Holes

From batter prepared in the method of Example 4, extrude batter through a doughnut press or any other desired device in rings onto hot oil; batter may also be dropped in balls, long pieces, even pretzel shapes. Temperature of the oil should be about 300–500 degrees.

If the oil is hot enough the dough will float at the top of the oil. Fry doughnuts or other shapes until golden brown on all sides. Remove from oil, drain. Serve plain or top with fruit, honey, nuts, coconut, peanut butter, etc.

Alternatively, doughnuts may be preparations of conventional ingredients including but not limited to other flours, extenders, binders, fillers, preserving agents, falvorings, seasonings, eggs, milk, and so forth.

EXAMPLE NUMBER 11

Malanga Dumplings

Prepare a dumpling batter in the method of example 5. Let dough set for about 15 minutes. Drop teaspoonsized portions of batter into about 2 liters of rapidly boiling water or broth, may be thickened. Allow to remain in boiling water 2–6 minutes, preferably 5 minutes. If dumplings remain in boiling broth longer, dumplings will dissolve. When done, dumplings will be light and tender on the inside.

EXAMPLE NUMBER 12

Malanga Batter

A batter prepared by the method of Example 4 may be used as batter for deep frying and for fondue cooking techniques Coat vegetables, fruit, or cooked meat in batter and deep fry in hot oil (preheated to medium-high heat). If the oil is hot enough the dough should float at the top of the oil. Test for proper temperature with a small ball of dough.

EXAMPLE NUMBER 13

Crepes

In yet another embodiment of the batter prepared in Example 4, the batter may be used to make a crepe-like product. The batter may be diluted by the addition of 10–400 g water, preferably 100 g to make a crepe-like product. The batter is spread in very thin layers on a cooking surface, and prepared according to the accepted convention.

EXAMPLE NUMBER 14

Malanga Pie Crust

Mix thoroughly, 168.5 g malanga flour, 50 g oil, 170 g boiling water. Shape into round, flat dough ball. By any conventional means, shape into appropriate dimensions for pie crust. Preferably, place between cellophane or wax paper sheets before rolling out dough. This dough is also very well suited to shaping in a mold; it can be reshaped many times without becoming hard and leathery.

Malanga pie crust may be used as a double or single crust pie, with any type of filling, including meat (e.g., chicken pot pie) or fruit filling. May be used baked or unbaked. For a baked pie crust, bake for 10 minutes at 350° F.

Although above ingredients are preferred, malanga flour may be used with shortening or lard and any other conventional ingredients. For example, when using lard, use about 100 g and decrease water to 10–14 g. Dough will seem stiff and hard, but will be just right after baking.

EXAMPLE NUMBER 15

Malanga Tortillas, Chips

Mix 168.5 g malanga flour with 170 g water; knead until well blended and very thick. By any desired conventional means achieve the shapes and sizes of tortillas or chips. May be fried with or without oil, or baked. When fried without oil, heat on medium high heat until slightly browned on both sides; turn as needed. When fried in hot oil, fry until crisp. Alternatively, bake by conventional means until crisp.

EXAMPLE NUMBER 16

Pretzels

Doughs produced by the processes described in Examples 14 and 15 may be used in processes of shaping to form pretzels of various sizes, coating with oil (optional), cooking by various processes of the art including but not limited to baking, frying, and drying to produce pretzels of varying sizes.

In alternative processes, pretzels may be produced in processes above into which are incorporated any combinations of processes including but not limited to additional flours, eggs, milk, flavorings, seasonings, binders, fillers, extenders, and preserving agents.

EXAMPLE 17

Malanga Imitation Nut Butter 453 grams of malanga flour are placed into any blending equipment suitable for mixing very thick doughs at very high speeds, to which is added 170–225 g edible fatty material, such a vegetable oils (preferred for hypoallergenic products) but could also include other fatty materials, and a gelatinized paste produced by cooking 21 g malanga flour and 113.25 g water. The materials ar intimately mixed for about 2 minutes or until the entire mixture is well blended, and the consistency of peanut butter.

EXAMPLE 18

Malanga Imitation Mayonnaise

Combine 52.6 g malanga flour, 6.5 g salt, and 113.25 g cold water until well blended. Add slowly to 340 g boiling water, stirring constantly. Continue stirring, while maintaining temperature at 50° to 150° C., until mixture is completely gelatinized and thickened. Place mixture in conventional high speed blending device; add 200 g oil, and optional: 21.3 g lemon juice, vinegar, or ascorbic acid solution. Mix materials on highest speed until well blended, smooth, and uniform consistency. Mayonnaise will thicken as it cools.

EXAMPLE NUMBER 19

Malanga Milk

Combine 453 g water and 42.1 g malanga flour, mix thoroughly. Stirring constantly, heat until well gelatinized, thick, and well blended. Blend together an additional 453 g water, 126.3 g very finely pulverized malanga flour, and 18.7 g oil in any high speed blending device. Add in the cooked flour mixture. Blend 1–30 minutes at highest speeds, preferably 4 minutes. May be strained if flour not sufficiently fine.

EXAMPLE NUMBER 20

Malanga Noodles

Using conventional equipment for kneading thick dough, combine 453 g flour and 340 g boiling water. Knead well until dough is well mixed and forms soft doughy clumps. Extrude to various shapes of macaroni, fettucine, spaghetti, lasagna and the like. Cut to desired lengths, dry by any conventional means, preferably air drying on trays, conveyors or the like. Dough may be used to make any pasta product common in the art including but not limited to ravioli, Chinese-style meat filled noodle dumplings, and other meat-filled products.

Alternatively a small amount of flour and water, preferably 20 g malanga flour and 120 g water may be cooked to a thick paste and added to the above mixture.

In another alternative process, prior to extruding, the flour mixture described above which may or may not be simultaneously kneaded, may be maintained at temperatures above 50° C. for 2–30 minutes, preferably 2–5 minutes at 95° C. to gelatinize part of all of the dough.

When cooking, immerse noodles in boiling water for 2–10 minutes depending on width of noodles. Any other cooking techniques of the art may also be used. Noodles will change from off-white opaque to light brown as the starch granules gelatinize.

Noodles may be used in any type pasta dish—soups, stews, pasta and sauce dishes, and the like.

EXAMPLE NUMBER 21

Malanga Crackers

In any suitable machine for mixing heavy doughs, combine 453 g malanga flour, 340 water, 6.5 g salt, 75 g oil, and 23.6 g baking powder. By any conventional means, including but not limited to molding, rolling, cutting, extruding, and the like, shape into desired shapes. Coat with a very thin film of oil, sprinkling with salt. Heat to 350° F. for 20 minutes. Otherwise, cook by any convention of the art, including baking, frying and the like.

Alternatively, omit oil, or oil and salt, increasing water by 30 grams.

Alternatively, use binders, flours, sweeteners, extenders, flavorings, seasonings, fillers and other ingredients common to the art to produce a hyperallergenic cracker.

EXAMPLE 22

Pudding

Combine equal parts by volume of cooked, mashed malanga and water, using 113.25 g of each. The method of cooking and pureeing may be by any conventional means including but not limited to steam heat, boiling and pressure cooking. The preferred method involves subjecting the peeled or unpeeled raw tubers, peeled tubers are preferred, to application of steam until all starch particles are gelatinized. The gelatinized tubers are comminuted to a thick paste by any conventional means. Separately, 5.25 g malanga flour is combined with 28.4 g water and heated to boiling point for sufficient time to produce a thick, gelatinized paste. The gelatinized paste is combined with the cooked tuber paste by any conventional mixing technique until well blended. The mixture is the consistency of pudding, and with the addition of no other ingredients has a pleasant, sweet taste. This is not to preclude the use of other ingredients commonly used as ingredients in pudding such as eggs, milk, conventional flours, oil, sweeteners, flavorants, spices, seasonings, of any kind in this invention.

Alternatively, combine 84.2 g malanga flour and 453 g water, heat the resultant mixture by any conventional means with stirring until the mixture is very thick and completely gelatinized. Place in high speed blending device and blend at highest setting for at least 5 minutes. Add 25 g oil and blend again for 1-2 minutes.

EXAMPLE 23

Malanga Flour

Peel malanga or other Arum tubers under running water, also removing any spots, undersirable areas, then free of excess water, dip briefly in distilled water, again remove excess do not soak. Shred to desired size, place on glass or metal trays; air dry at 145° F. for 8-12 hours, preferably 10. Pulverize shreds with any desired technique that utilizes 25% or more of the fiber, 100% utilization is preferred.

EXAMPLE 24

Cooked Malanga Flour

Malanga or other tubers are processed by the method of Example 23, with the added step of partially or completely gelatinizing the tubers as a separate step or in combination with other process steps.

Having now fully described the invention, it will be apparent to one of ordinary skill in the art that many changes and modifications can be made thereto without departing from the spirit of the invention as set forth herein.

What is claimed as new and so intended to be secured by Letters Patent is:

1. A non-grain edible malanga flour possessing the ability to maintain a risen structure in the absence of grain flour, legume flour, or added fiber, said non-grain edible flour consisting of comminuted particles of the entire malanga, including substantially all of the starch and fiber content of the malana, wherein said flour has a moisture content of less than 30% by weight.

2. The entire flour of claim 1 wherein the flour passes through a screen of 0.0001 inch mesh.

3. The flour of claim 1, wherein the malanga flour is uncooked.

4. The flour of claim 1, wherein the flour is at least partially gelatinized.

5. A baked product consisting essentially of, malanga flour, water and leavening agent wherein the malanga flour consists of the flour of claim 1, and wherein the flour is present in an amount of 1 part by weight, and the water is present in an amount of 0.5-4 parts by weight per weight of flour.

6. A colloidal product consisting essentially of, malanga flour, oil and water wherein the malanga flour consists of the flour of claim 1, and wherein the flour is present in an amount of 0.1-3 parts by weight, and the oil and water are each present in an amount of 1-15 parts by weight which may be the same or different.

7. A fried product consisting essentially of malanga flour, oil and water, wherein the malanga flour consists of the flour of claim 1.

8. An extruded product consisting essentially of malanga flour and water, wherein the malanga flour consists of the flour of claim 1.

9. A milk substitute consisting essentially of malanga flour and water and, wherein the malanga flour consists of the flour of claim 1 wherein the flour and water are present in proportions of 1:1 to 1:30 parts by weight of flour per weight of water.

10. An ice cream substitute formed by a process consisting essentially of the steps of freezing the milk substitute of claim 9.

11. An infant formula consisting essentially of malanga flour and water, wherein the malanga flour consists of the flour of claim 1.

12. An imitation nut butter product consisting essentially of malanga flour and oil wherein the malanga flour consists of the flour of claim 1.

13. A batter-type product consisting essentially of malanga, malanga flour,
an oil, and
water,
wherein the malanga flour consists of the flour of claim 1, and wherein the flour is present in an amount of 1 part by weight; and the water is present in an amount of 4.5-6 parts by weight and the oil is present in an amount of 0-½ part by weight.

14. A non-grain edible flour of malanga of family Araceae wherein the flour consists of the entire malanga, including all of the starch and fiber portions of said malanga, comminuted to a size so that said entire comminuted malanga will pass through a screen of 0.001 inch mesh, said flour having a moisture content of less than 20% by weight.

* * * * *